United States Patent
Nagano et al.

(10) Patent No.: US 8,410,164 B2
(45) Date of Patent: Apr. 2, 2013

(54) REAGENT FOR MEASUREMENT OF ACTIVE OXYGEN

(75) Inventors: Tetsuo Nagano, Tokyo (JP); Yasuteru Urano, Kanagawa (JP); Saki Izumi, Ibaraki (JP)

(73) Assignee: The University of Tokyo, Tokyo (JP)

( * ) Notice: Subject to any disclaimer, the term of this patent is extended or adjusted under 35 U.S.C. 154(b) by 22 days.

(21) Appl. No.: 12/991,750

(22) PCT Filed: May 15, 2009

(86) PCT No.: PCT/JP2009/059031
§ 371 (c)(1),
(2), (4) Date: Jun. 30, 2011

(87) PCT Pub. No.: WO2009/139452
PCT Pub. Date: Nov. 19, 2009

(65) Prior Publication Data
US 2011/0251404 A1    Oct. 13, 2011

(30) Foreign Application Priority Data
May 16, 2008   (JP) ................................ 2008-129024

(51) Int. Cl.
*A61K 31/352* (2006.01)
*C07D 311/82* (2006.01)

(52) U.S. Cl. ........ 514/454; 549/200; 549/223; 514/449; 514/453

(58) Field of Classification Search .................. 549/200, 549/223; 514/449, 453, 454
See application file for complete search history.

(56) References Cited

U.S. PATENT DOCUMENTS

| | | | |
|---|---|---|---|
| 6,525,088 B1 | 2/2003 | Nagano et al. | |
| 6,569,892 B2 * | 5/2003 | Nagano et al. | 514/455 |
| 7,087,766 B2 | 8/2006 | Nagano et al. | |
| 7,378,282 B2 | 5/2008 | Setsukinai et al. | |
| 7,868,147 B2 * | 1/2011 | Nagano et al. | 536/18.1 |
| 7,901,852 B2 * | 3/2011 | Garza et al. | 430/30 |
| 2003/0153027 A1 | 8/2003 | Nagano et al. | |
| 2009/0258434 A1 | 10/2009 | Nagano et al. | |
| 2009/0317914 A1 | 12/2009 | Nagano et al. | |

FOREIGN PATENT DOCUMENTS

| | | |
|---|---|---|
| WO | 99/51586 | 10/1999 |
| WO | 01/64664 | 9/2001 |
| WO | 2005/103282 | 11/2005 |
| WO | 2010/064443 | 6/2010 |

OTHER PUBLICATIONS

C. Beghetto et al., "Implications of the generation of reactive oxygen species by photoactivated calcein for mitochondrial studies", European Journal of Biochemistry, 2000, pp. 5585-5592.
T.W. Greene, "Protective Groups in Organic Synthesis", Third Ed. John Wiley & Sons, Inc., 1999, pp. v-xxi, and 368-405.
Saito, I. et al., J. Am. Chem. Soc., 1985, 107, pp. 6329-6334.
U.S. Appl. No. 13/131,173 to Tetsuo Nagano et al., filed Dec. 4, 2009.
English version of the International Preliminary Report on Patentability for International application No. PCT/JP2009/059031 dated Jan. 20, 2011.
Japanese version of the International Preliminary Report on Patentability for International application No. PCT/JP2009/059031 dated Nov. 25, 2010.
International Search Report for PCT/JP2009/059031, dated Jun. 9, 2009.

\* cited by examiner

*Primary Examiner* — Golam M Shameem
(74) *Attorney, Agent, or Firm* — Greenblum & Bernstein, P.L.C.

(57) ABSTRACT

A compound represented by the formula (I) ($R^1$ represents an aryl group such as hydroxyphenyl group, $R^2$ represents 2-carboxyphenyl group etc., and $R^3$ and $R^4$ represent —$(CH_2)_p$—$N(R^5)(R^6)$ ($R^5$ and $R^6$ represent —$(CH_2)_n$—COOH), a salt thereof, or an ester thereof, which is useful as a reagent for highly sensitive measurement of reactive oxygen such as hydroxy radical present at a trace amount in living bodies or tissues by a bioimaging technique over a long period of time.

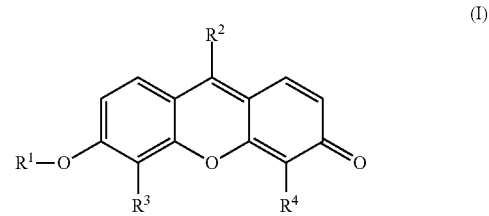

(I)

20 Claims, 5 Drawing Sheets

REAGENT FOR MEASUREMENT OF ACTIVE OXYGEN

TECHNICAL FIELD

The present invention relates to a compound or a salt thereof useful as a reagent for measurement of reactive oxygen. The present invention also relates to a reagent for measurement of reactive oxygen comprising the aforementioned compound or a salt thereof.

BACKGROUND ART

It is known that, in living bodies and life phenomena, free radical species such as nitrogen monoxide are acting as a second messenger for signal transduction, and that they exerts various physiological functions, for example, control of blood pressure in the circulatory system, and the like. Reactive oxygen, which is one type of free radical species, includes superoxide anion, hydrogen peroxide, hydroxyl radical, singlet oxygen, and the like. As for hydroxyl radical among them, there are many articles reporting that the radical is involved in vascular disorders or brain disorders after ischemia or DNA modification by ultraviolet, and is considered to be a reactive oxygen species having particularly high harmful nature in relation to causes and pathologies of diseases.

Elucidation of the role of reactive oxygen species in living bodies has thus become more and more important. However, there are many problems in methods for measurement of the species. As for methods for measurement of hydroxyl radical, various reports have been made on its measurement by the electron spin resonance (ESR) method. However, the ESR method has fundamental difficulty in using living cells as measurement samples, and practically, the measurement and the evaluation at an individual cell level are impossible. A method is also known in which DCFH-DA (2',7'-dichlorodihydrofluorescein diacetate, Molecular Probes, catalog No. D-399), which enables measurement of wide variety of reactive oxygen species, is used together with an inhibitor against generation of other reactive oxygen species, and hydroxyl radical is detected under a microscope. However, results obtained in the coexistence of the inhibitor include some factors different from those included in reactions in living bodies. In addition, DCFH-DA is very susceptible to autoxidation, and for this reason, background fluorescence by autoxidation interferes the detection when the same field needs to be observed several times. The method is also extremely inconvenient with respect to operability and storability considering that the method requires operations in the dark.

As reagents enabling convenient and highly sensitive measurement of reactive oxygen species, there have been provided reagents specific to singlet oxygen (International Patent Publication WO99/51586), and reagents enabling specific and highly sensitive measurement of hydroxyl radical, peroxynitrite, hypochlorous acid, and the like (as compounds, hydroxyphenylfluorescein (HPF), aminophenylfluorescein (APF), and the like, International Patent Publication WO01/64664, HPF and APF are sold by SEKISUI MEDICAL CO., LTD.). However, fluorescein produced by a reaction of the latter reagents with reactive oxygen species has poor intracellular retentivity, and may leak from the cells, and therefore it may become difficult to measure a trace amount of intracellular reactive oxygen by using said reagents.

PRIOR ART REFERENCES

Patent Documents

Patent document 1: International Patent Publication WO99/51586
Patent document 2: International Patent Publication WO01/64664

SUMMARY OF THE INVENTION

Object to be Achieved by the Invention

An object of the present invention is to provide a compound useful as a reagent for measurement of reactive oxygen such as hydroxyl radical. Another object of the present invention is to provide a reagent for measurement of reactive oxygen comprising said compound and a method for measurement of reactive oxygen using said compound. In particular, it is an object of the present invention to provide a reagent for highly sensitive measurement of reactive oxygen present at an extremely small amount in living bodies or tissues, more specifically, reactive oxygen present at a trace amount in cells, by a bioimaging technique over a long period of time.

Means for Achieving the Object

The inventors of the present invention conducted various studies to achieve the foregoing objects. As a result, they found that substantially non-fluorescent compounds represented by the following general formula (I) efficiently reacted with reactive oxygen such as hydroxyl radical under a physiological condition to give a dearylated fluorescent compound, and that the dearylated fluorescent compound produced from the compound represented by the general formula (I) had extremely high intracellular retentivity, and the compound represented by the general formula (I) was thus extremely useful as a reagent for highly sensitive measurement of a trace amount of reactive oxygen existing in cells. The present invention was accomplished on the basis of these findings.

The present invention thus provides a compound represented by the following general formula (I):

[Formula 1]

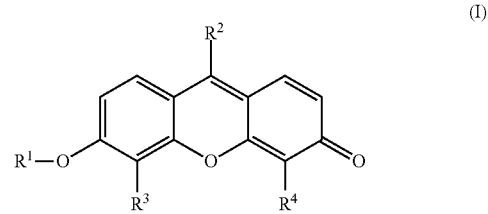

wherein $R^1$ represents an aryl group which may be substituted, $R^2$ represents a 2-carboxyphenyl group which may be substituted, and $R^3$ and $R^4$ independently represent a group represented as —$(CH_2)_p$—$N(R^5)(R^6)$ (in the formula, p represents an integer of 1 to 4, and $R^5$ and $R^6$ independently represent —$(CH_2)_n$—COOH (in the formula, n represents an integer of 1 to 4)), a salt thereof, or an ester thereof.

According to preferred embodiments of the present invention, there are provided the aforementioned compound, a salt thereof, or an ester thereof, wherein $R^1$ is a phenyl group substituted with amino group or hydroxyl group; the aforementioned compound, a salt thereof, or an ester thereof, wherein $R^1$ is p-aminophenyl group or p-hydroxyphenyl group; the aforementioned compound, a salt thereof, or an ester thereof, wherein $R^2$ is 2-carboxyphenyl group; the aforementioned compound, a salt thereof, or an ester thereof, wherein $R^3$ and $R^4$ represent —$(CH_2)$—$N[(CH_2)$—$COOH]_2$; the aforementioned compound, a salt thereof, or an ester thereof, wherein $R^1$ is p-aminophenyl group or p-hydroxyphenyl group, $R^2$ is 2-carboxyphenyl group, and $R^3$ and $R^4$ represent —$(CH_2)$—$N[(CH_2)$—$COOH]_2$; and an ester of the aforementioned compound, wherein the ester is a tetracetoxymethyl ester formed with $R^3$ or $R^4$.

From another aspect, the present invention provides a reagent for measurement of active oxygen, which comprises a compound represented by the aforementioned general formula (I), a salt thereof, or an ester thereof.

According to preferred embodiments of this invention, there are provided the aforementioned reagent, which is a reagent for measurement of a highly reactive oxygen species; and the aforementioned reagent, wherein the reactive oxygen species is hydroxyl radical, peroxynitrite, or hypochlorous acid.

The present invention further provides a method for measurement of reactive oxygen, which comprise the following steps: (A) the step of reacting a compound of the aforementioned formula (I) or a salt thereof with reactive oxygen, and (B) the step of measuring fluorescence of a dearylated compound (compound of the aforementioned formula (I) wherein $R^1$ is hydrogen atom) or a salt thereof produced in the above step (A).

According to preferred embodiments of this invention, there are provided the aforementioned method wherein a reagent for measurement of a highly reactive oxygen species is used; and the aforementioned method wherein the reactive oxygen species is hydroxyl radical, peroxynitrite, or hypochlorous acid.

Effect of the Invention

The compound of the present invention is useful as a reagent for measurement of a reactive oxygen species, preferably a highly reactive oxygen species (for example, hydroxyl radical, peroxynitrite or hypochlorous acid). The fluorescent substance produced by a reaction of the compound with a reactive oxygen species has extremely high intracellular retentivity. Accordingly, said compound has a superior characteristic feature that it enables extremely highly sensitive measurement of a trace amount of a reactive oxygen species existing in cells over a long period of time. A reagent for measurement of reactive oxygen comprising the compound of the present invention and a method for measurement of reactive oxygen using the aforementioned compound are useful as a reagent and a method for measuring, in particular, reactive oxygen localizing in specific cells or tissues of living bodies, with high sensitivity by a bioimaging technique.

MODES FOR CARRYING OUT THE INVENTION

Figure 1:
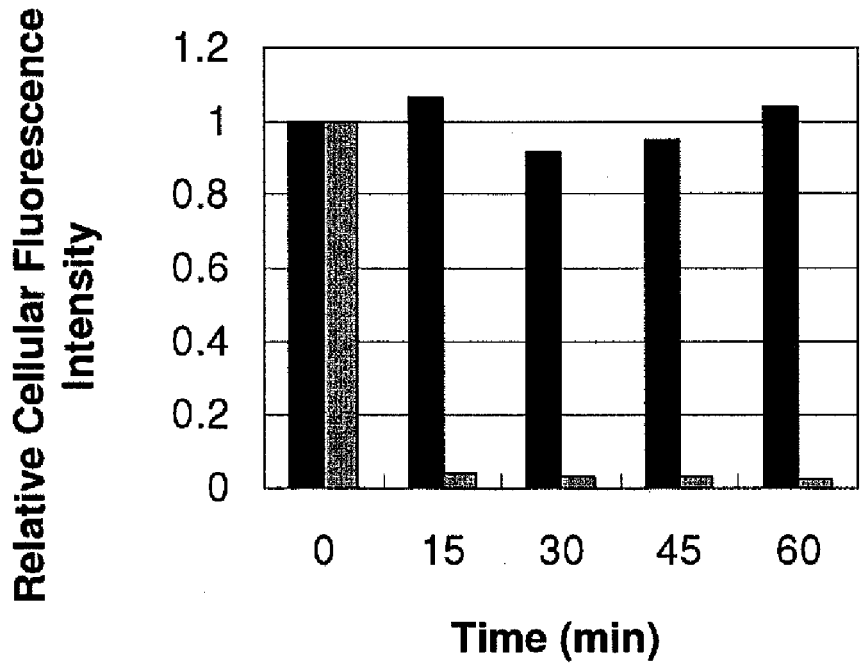
FIG. 1 shows the results of comparison of intracellular retentivity of calcein (left bars) and fluorescein (right bars) measured by using HL-60 (upper graph), and results of comparison of $pK_a$ (lower graph, the right plotted curve represents the results for fluorescein).
Figure 1:
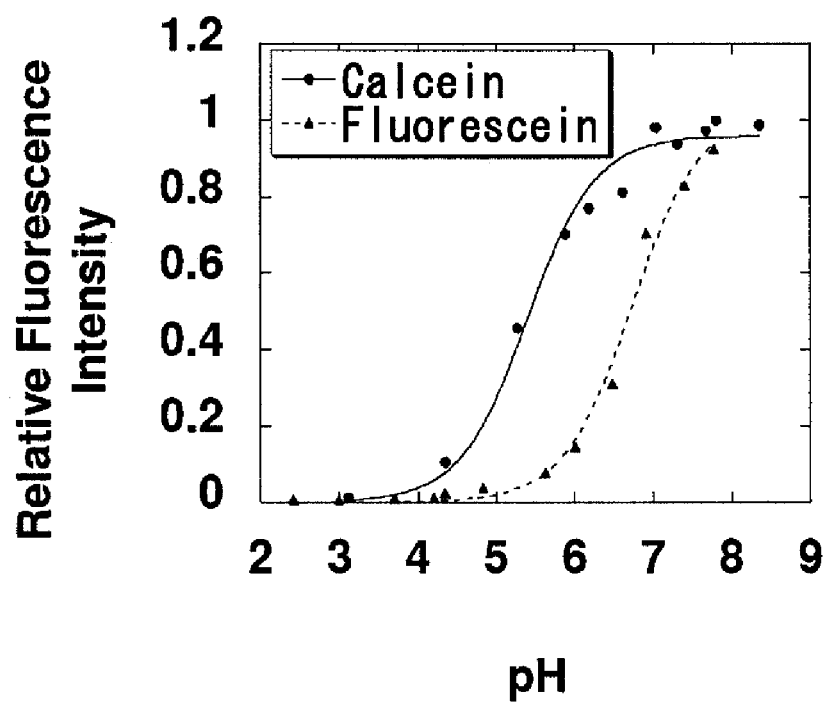

As the aryl group represented by $R^1$, for example, a monocyclic, bicyclic, or tricyclic aryl group having 6 to 14 ring-constituting atoms can be used. Preferably a phenyl group or a naphthyl group, and more preferably a phenyl group can be used. The aryl group may have one or more substituents on the ring. When the aryl group has two or more substituents, they may be the same or different. The type and substituting position of the substituent are not particularly limited. For example, a $C_{1-6}$ alkyl group (the alkyl group may be any of linear, branched, and cyclic alkyl groups, or a combination thereof, and the same shall apply to an alkyl moiety of other substituents having the alkyl moiety), a $C_{1-6}$ haloalkyl group, a $C_{1-6}$ alkenyl group, a $C_{1-6}$ alkoxy group, a halogen atom (the halogen atom may be any of fluorine atom, chlorine atom, bromine atom, and iodine atom), cyano group, nitro group, an optionally substituted amino group, carboxyl group, an alkoxycarbonyl group, a $C_{1-6}$ alkanoyl group, a $C_{1-6}$ haloalkanoyl group, an aroyl group, hydroxy group, an alkylenedioxy group, and the like may be used as the substituent.

$R^1$ is preferably a substituted phenyl group, and a monosubstituted phenyl group is more preferred. As the monosubstituted phenyl group, a phenyl group having non-substituted amino group or hydroxy group is particularly preferred. The substituting position of the substituent is preferably the ortho-position or para-position. As $R^1$, p-aminophenyl group or p-hydroxyphenyl group is particularly preferred.

The benzene ring of 2-carboxyphenyl group represented by $R^2$ may have one or more substituents. When the benzene ring has two or more substituents, they may be the same or different. The groups explained for the aforementioned aryl group can be used as a substituent on the benzene ring, and $R^2$ is preferably a non-substituted 2-carboxyphenyl group.

In $-(CH_2)_p-N(R^5)(R^6)$ represented by $R^3$ or $R^4$, p represents an integer of 1 to 4, preferably an integer of 1 to 3, more preferably 1 or 2, most preferably 1. $R^5$ and $R^6$ independently represent $-(CH_2)_n-COOH$, and n represents an integer of 1 to 4, preferably an integer of 1 to 3, more preferably 1 or 2, and most preferably 1.

The compound represented by the general formula (I) may exist as a salt. Examples of the salt include a base addition salt, an acid addition salt, and an amino acid salt. Examples of the base addition salt include: metal salts such as sodium salts, potassium salts, calcium salts, and magnesium salts; ammonium salts; and organic amine salts such as triethylamine salts, piperidine salts, and morpholine salts. Examples of the acid addition salt include: mineral acid salts such as hydrochlorides, sulfates, and nitrates; and organic acid salts such as methanesulfonates, p-toluenesulfonates, citrates, and oxalates. Examples of the amino acid salt include glycine salts. However, salts of the compounds of the present invention are not limited to these examples. Among them, physiologically acceptable water-soluble salts can be suitably used for the reagent and the measurement method of the present invention.

As an esterified compound represented by general formula (I); a compound wherein any one or two or more of carboxy groups selected from the group consisting of a carboxy group in R2 in the form of 2-carboxyphenyl group and carboxy groups existing by twos in each of R3 and R4 are esterified, can be used; more preferably, a compound wherein any one or two or more of carboxy groups selected from the group consisting of a total of four carboxy groups existing by twos in each of R3 and R4 are esterified, can be used; furthermore preferably, a compound wherein three or more of carboxy groups selected from the group consisting of a total of four carboxy groups existing by twos in each of R3 and R4 are esterified, can be used; and most preferably, a compound wherein a total of four carboxy groups existing by twos in each of R3 and R4 are all esterified, can be used. When the compound contains two or more ester groups, the ester residues may be the same or different.

As the ester, a physiologically acceptable ester is preferred. Preferred examples of ester residue include, for example, methyl group, ethyl group, propyl group, isopropyl group, butyl group, isobutyl group, t-butyl group, benzyl group, acetoxymethyl group, 1-(acetoxy)ethyl group, propionyloxymethyl group, 1-(propionyloxy)ethyl group, butyryloxymethyl group, 1-(butyryloxy)ethyl group, isobutyryloxymethyl group, 1-(isobutyryloxy)ethyl group, valeryloxymethyl group, 1-(valeryloxy)ethyl group, isovaleryloxymethyl group, 1-(isovaleryloxy)ethyl group, pivaloyloxymethyl group, 1-(pivaloyloxy)ethyl group, methoxycarbonyloxymethyl group, 1-(methoxycarbonyloxy)ethyl group, ethoxycarbonyloxymethyl group, 1-(ethoxycarbonyloxy)ethyl group, propoxycarbonyloxymethyl group, 1-(propoxycarbonyloxy)ethyl group, isopropoxycarbonyloxymethyl group, 1-(isopropoxycarbonyloxy)ethyl group, butoxycarbonyloxymethyl group, 1-(butoxycarbonyloxy)ethyl group, isobutoxycarbonyloxymethyl group, 1-(isobutoxycarbonyloxy)ethyl group, t-butoxycarbonyloxymethyl group, 1-(t-butoxycarbonyloxy)ethyl group, cyclopentanecarbonyloxymethyl group, 1-(cyclopentanecarbonyloxy)ethyl group, cyclohexanecarbonyloxymethyl group, 1-(cyclohexanecarbonyloxy)ethyl group, cyclopentyloxycarbonyloxymethyl group, 1-(cyclopentyloxycarbonyloxy)ethyl group, cyclohexyloxycarbonyloxymethyl group, 1-(cyclohexyloxycarbonyloxy)ethyl group, benzoyloxymethyl group, 1-(benzoyloxy)ethyl group, phenoxycarbonyloxymethyl group, 1-(phenoxycarbonyloxy)ethyl group, (5-methyl-2-oxo-1,3-dioxolen-4-yl)methyl group, 2-trimethylsilylethyl group, and the like, but the examples are not limited to these.

The compound represented by the formula (I) in free form, a salt thereof, or an ester thereof may exist as a hydrate or solvate, and all of these substances fall within the scope of the present invention. The type of solvent that forms the solvate is not particularly limited. For example, solvents such as ethanol, acetone and isopropanol can be exemplified.

The compound represented by the general formula (I) may have one or more asymmetric carbons depending on the type of the substituent, and stereoisomers such as optical isomers or diastereoisomers may exist. These stereoisomers in pure forms, any mixtures of these stereoisomers, racemates and the like all fall within the scope of the present invention. In addition, the carboxy group of 2-carboxyphenyl group in the compound represented by formula (I) may form a lactone ring in the molecule. It should be understood that such compounds in which a lactone ring is formed also fall within the scope of the present invention. Optically active substances due to the aforementioned lactone formation also fall within the scope of the present invention.

The compound of the present invention represented by the general formula (I) can be prepared generally by introducing $R^3$ and $R^4$ into a corresponding fluorescein compound to prepare a compound wherein $R^1$ is hydrogen atom, and then arylating this compound. Means for alylation is specifically described in International Patent Publication WO01/64664, and the like. For example, an alkali metal salt of a fluorescein compound can be prepared beforehand, and then the salt can be reacted with an aryl iodide compound in a suitable solvent. Methods for preparation of typical compounds represented by the general formula (I) of the present invention are shown in the examples described in this specification. Accordingly, one of ordinary skill in the art can readily prepare the compounds of the present invention by suitably choosing a starting material and a reaction reagent based on the specific explanations in the examples and appropriately altering or modifying reaction conditions and steps, if necessary.

In addition, a target compound may be efficiently prepared by performing the reaction with optionally protecting a particular class of functional group in the reaction steps. Detailed explanations of protective groups are given in, for example, Protective Groups in Organic Synthesis, T. W. Greene, John Wiley & Sons, Inc., 1981, and the like, and one of ordinary skill in the art can choose suitable protective groups.

In the above preparation methods, isolation and purification of the products can be performed by an appropriate combination of techniques used in ordinary organic synthesis, for example, filtration, extraction, washing, dehydration, concentration, crystallization, various chromatography techniques and the like. The synthetic intermediates in the aforementioned steps can also be used for the subsequent reaction without particular purification. Where a salt of the compound of the present invention is prepared, when a salt of each compound is obtained in the above preparation method, the resulting salt, per se, may be purified, and when a compound in a free form is obtained, the compound in a free form can be dissolved or suspended in a suitable solvent and thereto added a base to form a salt, and the resulting salt may be purified, if necessary.

The compound of the present invention represented by the general formula (I) or a salt thereof has a property that it reacts with a reactive oxygen under a mild condition, for example, a physiological condition, to give a dearylated fluorescein compound (corresponding to a compound represented by the general formula (I) in which $R^1$ is hydrogen atom) or a salt thereof. The compound represented by the general formula (I) or a salt thereof is substantially non-fluorescent, whereas the dearylated fluorescein compound or a salt thereof has a property of emitting highly intense fluorescence. Therefore, by reacting a compound represented by the general formula (I) or a salt thereof with reactive oxygen, and then measuring fluorescence of the dearylated compound or a salt thereof, the reactive oxygen can be selectively measured with high sensitivity. This reaction scheme is specifically explained in International Patent Publication WO01/64664.

Although an ester of the compound represented by general formula (I) per se may not have the property of reacting with reactive oxygen to give a fluorescent substance, the ester may be converted into a compound represented by the general formula (I), for example, by cleavage of the ester with a hydrolase after said ester passes through a cell membrane and moves into a cell, and the produced compound represented by the general formula (I) reacts with reactive oxygen to give a fluorescence substance. Therefore, an ester of the compound represented by the general formula (I) can be used as a cell membrane-permeable reagent for measurement of reactive oxygen.

The type of reactive oxygen measurable with the reagent of the present invention is not particularly limited. For example, any of superoxide anion, hydroxyl radical, singlet oxygen, hydrogen peroxide and the like can be measured. In particular, highly reactive oxygen species (for example, hydroxyl radical, peroxynitrite, hypochlorous acid, and the like) can be measured with high sensitivity and selectivity. For example, when the compound represented by the general formula (I) or a salt thereof is used as a reagent for measurement of reactive oxygen, reactive oxygen localizing in an individual cell or a particular class of tissue can be accurately and conveniently measured.

The term "measurement" used in the present specification should be construed in its broadest sense, including determinations, tests, and detections performed for the purpose of quantification, qualification, diagnosis or the like. The method for measurement of reactive oxygen of the present invention generally comprises (A) the step of reacting a compound represented by the general formula (I) or a salt thereof with reactive oxygen; and (B) the step of measuring fluorescence of a dearylated compound produced in the above step (A) (corresponding to a compound represented by general formula (I) in which $R^1$ is hydrogen atom) or a salt thereof. When an ester of the compound represented by aforementioned general formula (I) is used, the reaction of the aforementioned step (A) advances with a compound represented by the general formula (I) or a salt thereof generated by hydrolysis of the ester compound that has passed through a cell membrane.

The fluorescence of the dearylated compound or a salt thereof may be measured by a conventional method. A method for measuring a fluorescence spectrum in vitro, a method for measuring a fluorescence spectrum in vivo by using a bioimaging technique and the like may be employed. For example, when quantification is performed, it is preferable to prepare a calibration curve beforehand according to a conventional method. As a quantitative hydroxyl radical generation system, for example, a gamma-radiolysis method and the like can be used. As a singlet oxygen generation system, for example, the naphthalene endoperoxide system (Saito, I, et. al., J. Am. Chem. Soc., 107, pp. 6329-6334, 1985) and the like can be used. An ester of the compound represented by the general formula (I) of the present invention has a property of passing through a cell membrane and being taken up into cells, and accordingly, it enables measurement of reactive oxygen localized in individual cells with high sensitivity by a bioimaging technique.

The compound represented by the aforementioned formula (I), a salt thereof, or an ester thereof per se may be used as the reagent for measurement of reactive oxygen of the present invention. However, if necessary, the compound may be used in the form of composition which is formulated with additives commonly used for preparation of a reagent. For example, additives such as solubilizing aids, pH adjusters, buffers, and isotonic agents can be used as additives for use of the reagent in a physiological condition, and amounts of these additives can be suitably chosen by one of ordinary skill in the art. The compositions may be provided as compositions in appropriate forms, for example, powdery mixtures, lyophilized products, granules, tablets, solutions and the like.

EXAMPLES

The present invention will be more specifically explained with reference to examples. However, the scope of the present invention is not limited to the following examples.

Example 1

A compound of the present invention was prepared according to the following scheme.

[Formula 2]
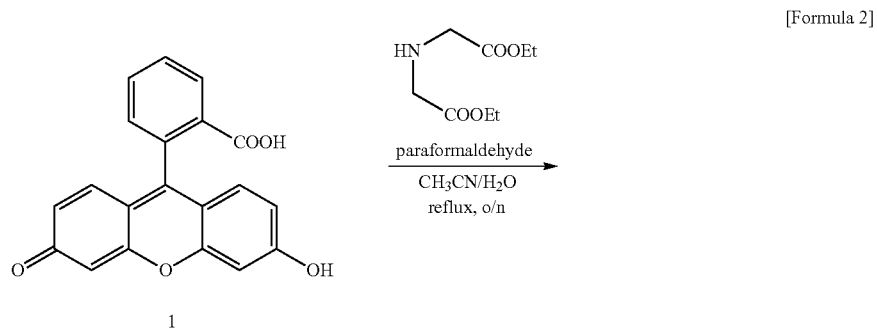
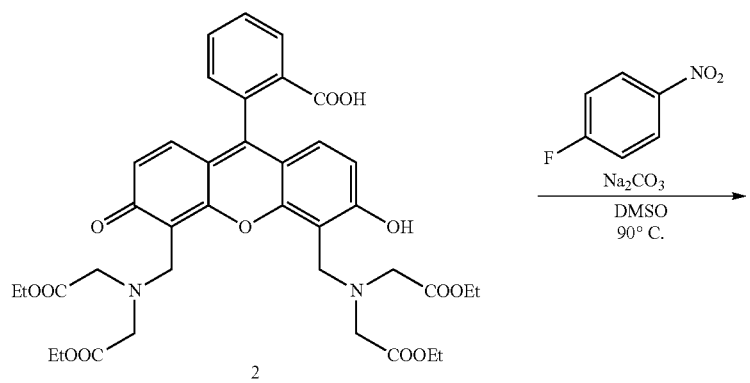
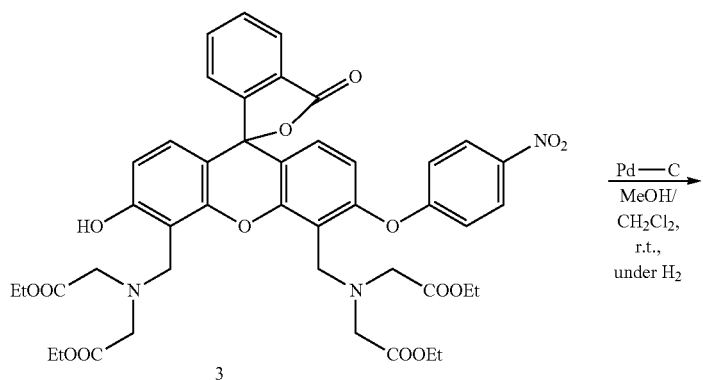
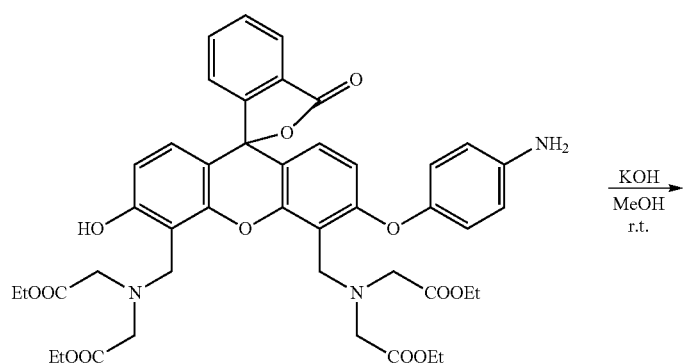

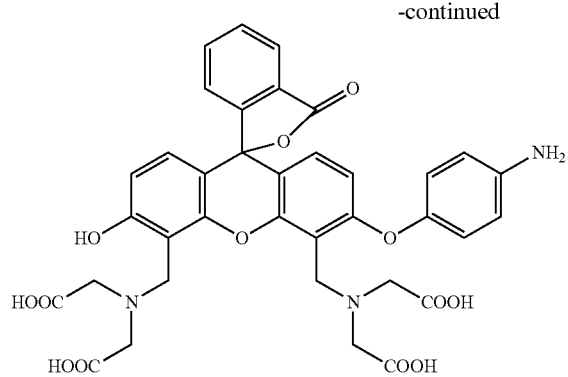
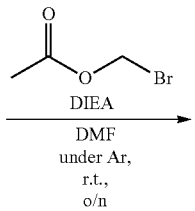

5 (APC)

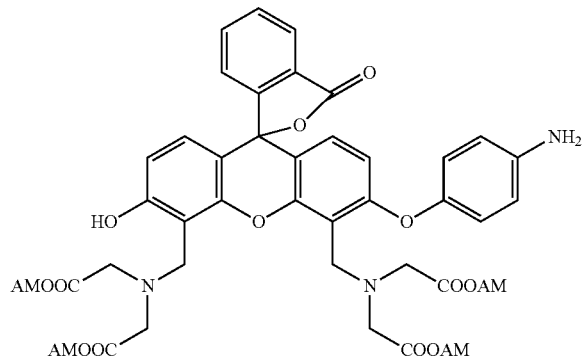

6 (APC-AM)

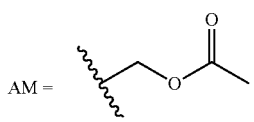

3,6-Dihydroxy-4,5-bis-[N,N'-di(carboxymethyl)aminomethyl]fluorescein tetraethyl ester (2)

Fluorescein 1 (1.01 g, 3.04 mmol), diethyl iminodiacetate (1.6 mg, 9.1 mmol) and paraformaldehyde (0.31 g, 10.3 mmol) were suspended in a mixed solution of acetonitrile (35 ml) and water (15 ml), and the suspension was refluxed by heating for 24 hours. The suspension was left to cool to room temperature, then the solvent was removed under reduced pressure, and the residue was purified by silica gel column chromatography (developing solvent: 1,2-dichloroethane) to obtain the compound 2 (2.078 g, yield: 93.1%) as pale yellow powder.

3-Hydroxy-4,5-bis-[N,N'-di(carboxymethyl)aminomethyl]-6-(4'-nitro)-phenoxyfluorescein tetraethyl ester (3)

The compound 2 (1.345 g, 1.83 mmol), 4-fluoronitrobenzene (0.29 g, 2.06 mmol) and sodium carbonate (0.58 g, 5.5 mmol) were dissolved in dimethyl sulfoxide (DMSO, 5 ml), and the solution was refluxed by heating for 8 hours. The solution was left to cool to room temperature, then neutralized with 2 N hydrochloric acid, and extracted with 1,2-dichloroethane/saturated brine. The organic layer was collected, dried over sodium sulfate, and filtered, and then the solvent was evaporated to obtain the unpurified compound 3. This was purified by NH silica gel column chromatography (developing solvent: n-hexane/1,2-dichloroethane) to obtain the compound 3 (251.6 mg, yield: 19.4%) as yellow solid.

6-(4'-Amino)phenoxy-3-hydroxy-4,5-bis[N,N'-di(carboxymethyl)aminomethyl]fluorescein tetraethyl ester (4)

The compound 3 (363.1 mg, 0.424 mmol) and 10% Pd—C (23.6 mg) were added to methanol/1,2-dichloroethane (1:9, 10 ml), the atmosphere was substituted with hydrogen gas, and catalytic reduction was carried out for 1 hour. The catalyst was removed by filtration, the solvent was evaporated, and then the residue was roughly purified by silica gel chromatography (developing solvent: 1,2-dichloroethane/methanol) and then purified by HPLC to obtain the compound 4 (252.6 mg, yield: 72.1%) as pale yellow powder.

3-Hydroxy-4,5-bis[N,N'-di(carboxymethyl)aminomethyl]-6-(4'-nitro)phenoxyfluorescein (Compound 5, APC)

The compound 4 (42.2 mg, 0.05 mmol) was dissolved in a 1 N solution of potassium hydroxide in methanol (40 ml), and the solution was stirred for 12 hours. The solution was neutralized with 2 N aqueous HCl, then the solvent was evaporated, and the residue was purified by HPLC to obtain the compound 5 (24.5 mg, yield: 67.2%) as pale yellow powder.

3-Hydroxy-4,5-bis[N,N'-di(carboxymethyl)aminomethyl]-6-(4'-nitro)phenoxyfluorescein tetracetoxymethyl ester (Compound 6, APC-AM)

The compound 5 (23.1 mg, 0.03 mmol), diisopropylethylamine (DIEA, 167.5 mg, 1.3 mmol), and bromomethyl acetate (198.9 mg, 1.3 mmol) were dissolved in dimethylformamide (5 ml), the atmosphere was substituted with argon, and the solution was stirred for 12 hours. The solution was extracted with ethyl acetate and a sodium phosphate buffer (Na—Pi buffer, pH 7.4). The organic layer was collected, dried over sodium sulfate, and filtered, then the solvent was evaporated, and the residue was purified by HPCL to obtain the compound 6 (6.8 mg, 21.0%) as white powder.

Compound 5 (APC)
$^1$H-NMR (400 MHz, DMSO-$d_6$)
δ 8.00 (d, 1H, J=7.6), 7.83-7.71 (m, 2H), 7.32 (d, 2H, J=7.2), 7.15 (d, 2H, J=7.2), 7.03 (d, 2H, J=8.8), 6.74 (d, 1H, J=8.8), 6.66 (d, 1H, J=8.8), 6.63 (d, 1H, J=8.8), 6.54 (d, 1H, J=8.8), 4.44-4.32 (m, 4H), 3.75 (s, 4H), 3.71 (s, 4H)
$^{13}$C-NMR (400 MHz, DMSO-$d_6$)
δ 171.7, 171.6, 168.7, 159.3, 158.5, 158.2, 157.4, 152.5, 150.8, 149.9, 135.8, 130.3, 128.9, 128.6, 125.7, 124.9, 124.1, 122.1, 120.3, 118.1, 115.2, 113.9, 113.0, 112.8, 109.3, 82.6, 54.1, 53.8, 47.4, 46.3
HRMS (ESI$^+$): m/z calcd for (M+H)$^+$, 714.19351; found, 714.19434.

Compound 6 (APC-AM)
$^1$H-NMR, (300 MHz, DMSO-$d_6$)
δ 8.49 (d, 1H, J=7.3), 7.71-7.59 (m, 2H), 7.24 (d, 2H, J=7.7), 6.8 (d, 2H, J=8.2), 6.65 (d, 2H, J=8.6), 6.61 (s, 2H), 6.56 (d, 1H, J=9.0), 6.36 (d, 1H, J=9.0), 5.83-5.80 (m, 4H), 5.65 (s, 4H), 4.62 (d, 1H, J=8.8), 4.42 (d, 1H, J=14.1), 4.32 (d, 1H, J=12.6), 4.32 (d, 1H, J=9.5), 4.30 (d, 1H, J=11.0), 3.88 (s, 4H), 3.73 (d, 4H, J=4.8), 2.08 (s, 6H), 2.03 (s, 6H)
HRMS (ESI$^-$): m/z calcd for (M−H), 1000.26238; found, 1000.26361.

Example 2

The compound 5 (APC) is a substantially non-fluorescent (Φf=0.007) substance having a moiety that specifically reacts with reactive oxygen species in the molecule. This substance specifically reacts with reactive oxygen species, and thereby becomes calcein to emit fluorescence. The tetracetoxymethyl ester of this calcein and diacetyl ester of fluorescein were taken up by HL-60 cells, and intracellular retentivity of calcein and fluorescein was evaluated. The results are shown in FIG. 1 (upper graph). It can be seen that the fluorescence intensity of calcein in the HL-60 cells (left bars) hardly decreased even after 60 minutes, whereas the fluorescence intensity of fluorescein in the HL-60 cells (right bars) decreased to a level of 1/10 or lower even after 15 minutes. The decrease of fluorescence intensity of fluorescein was due to leakage of fluorescein out of the cells, and it was demonstrated that calcein gave extremely superior intracellular retentivity. The conventional fluorescent probes for measurement of reactive oxygen, HPF and APF (SEKISUI MEDICAL CO., LTD.), react with reactive oxygen species and thereby become fluorescein to emit fluorescence, but $pK_a$ of fluorescein is 6.4, and therefore they have a problem that stability of fluorescence intensity is poor under a physiological condition. In contrast, $pK_a$ of calcein produced from APC is about 5.4 (FIG. 1, lower graph), and the fluorescence intensity thereof is stable at a physiological pH, and is extremely high (Φf=0.793). Thus, it was demonstrated that use of APC enabled observation with high sensitivity over a long period of time, which was not be achievable with the conventional probes for measurement of reactive oxygen.

Example 3

The compound 5 (APC) was reacted with various reactive oxygen species, and change of fluorescence spectrum was measured. The measurement was performed as follows.
(1) Hydroxyl Radical
To a 10 μM solution of APC in a phosphate buffer (0.1 M, pH 7.4, containing 0.02% DMF as a cosolvent) vigorously stirred at room temperature in a flask, 1 M aqueous hydrogen peroxide was added at a final concentration of 1 mM, and then aqueous iron(II) perchlorate was added dropwise to the mixture at a final concentration of 0 μM, 50 μM, 100 μM, 200 μM, 300 μM, 500 μM, 1000 μM, or 2000 μM. Immediately after the addition, fluorescence spectrum obtained with an excitation light of 494 nm was measured by using a fluorophotometer.
(2) Peroxynitrite
To a 10 μM solution of APC in a phosphate buffer (0.1 M, pH 7.4, containing 0.02% DMF as a cosolvent) stirred at 37° C. in a cuvette, a solution of peroxynitrite in 0.1 N aqueous sodium hydroxide was added dropwise at a final concentration of 0 μM, 1 μM, 2 μM, 3 μM, 4 μM, 5 μM, or 10 μM. After 30 minutes, fluorescence spectrum obtained with an excitation light of 494 nm was measured by using a fluorophotometer.
(3) Hypochlorous Acid
To a 10 μM solution of APC in a phosphate buffer (0.1 M, pH 7.4, containing 0.02% DMF as a cosolvent) stirred at 37° C. in a cuvette, a solution of sodium hypochlorite in 0.1 N aqueous sodium hydroxide was added dropwise at a final concentration of 0 μM, 1 μM, 2 μM, 3 μM, 4 μM, 5 μM, or 10 μM. After 30 minutes, fluorescence spectrum obtained with an excitation light of 494 nm was measured by using a fluorophotometer.
(4) Singlet Oxygen
To a 10 μM solution of APC in a phosphate buffer (0.1 M, pH 7.4, containing 0.02% DMF as a cosolvent) stirred at 37° C. in a cuvette, a solution of a singlet oxygen releasing agent EP-1 (3-(1,4-dihydro-1,4-epidioxy-1-naphthyl)propionic acid), which is known to heat-dependently release singlet oxygen, in DMF was added at a final concentration of 100 μM, and after 30 minutes, fluorescence spectrum obtained with an excitation light of 494 nm was measured by using a fluorophotometer.
(5) Superoxide
To a 10 μM solution of APC in a phosphate buffer (0.1 M, pH 7.4, containing 0.02% DMF as a cosolvent) stirred at 37° C. in a cuvette, an aqueous solution of xanthine oxidase was added at a final concentration of 10 μM, and then a solution of xanthine in DMF was added at a final concentration of 10 μM. After 30 minutes, fluorescence spectrum obtained with an excitation light of 494 nm was measured by using a fluorophotometer.
(6) Hydrogen Peroxide
To a 10 μM solution of APC in a phosphate buffer (0.1 M, pH 7.4, containing 0.02% DMF as a cosolvent) stirred at 37° C. in a cuvette, aqueous hydrogen peroxide was added at a final concentration of 100 μM, and after 30 minutes, fluorescence spectrum obtained with an excitation light of 494 nm was measured by using a fluorophotometer.
(7) Nitrogen Monoxide
To a 10 μM solution of APC in a phosphate buffer (0.1 M, pH 7.4, containing 0.02% DMF as a cosolvent) stirred at 37° C. in a cuvette, NOC-13 (1-hydroxy-2-oxo-3-(3-aminopropyl)-3-ethyl-1-triazene, nitrogen monoxide releasing agent) was added at a final concentration of 10 μmol/L, and after 30 minutes, fluorescence spectrum obtained with an excitation light of 494 nm was measured by using a fluorophotometer.

Figure 2:
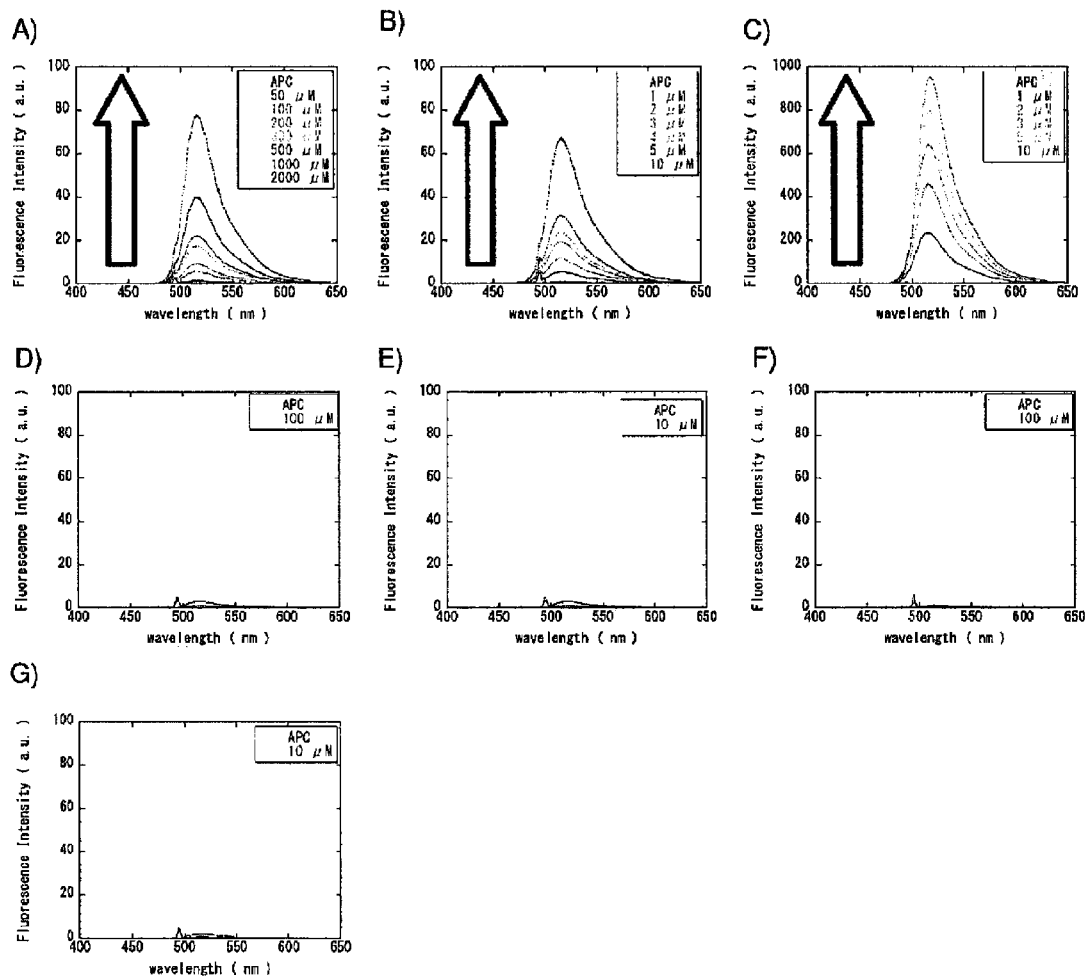
FIG. 2 shows reactivity of APC with reactive oxygen species or nitrogen species. The graphs show the results with (A) hydroxyl radical, (B) peroxynitrite, (C) hypochlorous acid, (D) singlet oxygen, (E) superoxide, (F) hydrogen peroxide, and (G) nitrogen monoxide.

The results are shown in FIG. 2. In FIG. 2, the graphs (A) to (G) show the results for the substances as follows: (A) hydroxyl radical, (B) peroxynitrite, (C) hypochlorous acid, (D) singlet oxygen, (E) superoxide, (F) hydrogen peroxide, and (G) nitrogen monoxide. It was confirmed that APC quickly reacted with, in particular, highly reactive oxygen species (hROS) such as hydroxyl radical, peroxynitrite and hypochlorous acid to give concentration-dependent increase of the fluorescence intensity thereof. On the other hand, it was confirmed that APC did not react with singlet oxygen, superoxide, hydrogen peroxide, and nitrogen monoxide, and no increase of fluorescence intensity occurred. Moreover, in order to confirm that the increase of fluorescence intensity was due to calcein produced by the reaction of APC with the reactive oxygen species, APC, the reaction mixture of APC and hypochlorous acid, and calcein were analyzed by HPLC under the following conditions.

Analysis Conditions

Elution solvent: A=$H_2O$/0.1% trifluoroacetic acid, B=80% acetonitrile/20% water/0.1% trifluoroacetic acid Analysis was started with A/B=95/5, and after 5 minutes, a linear gradient procedure was started and the ratio of A/B was changed to 20/80 in 30 minutes period.

Detection: fluorescence (ex./em.=470 nm/525 nm)

Column: ODS-3, 4.6×250 mm

Flow rate: 1 mL/minute

Figure 3:
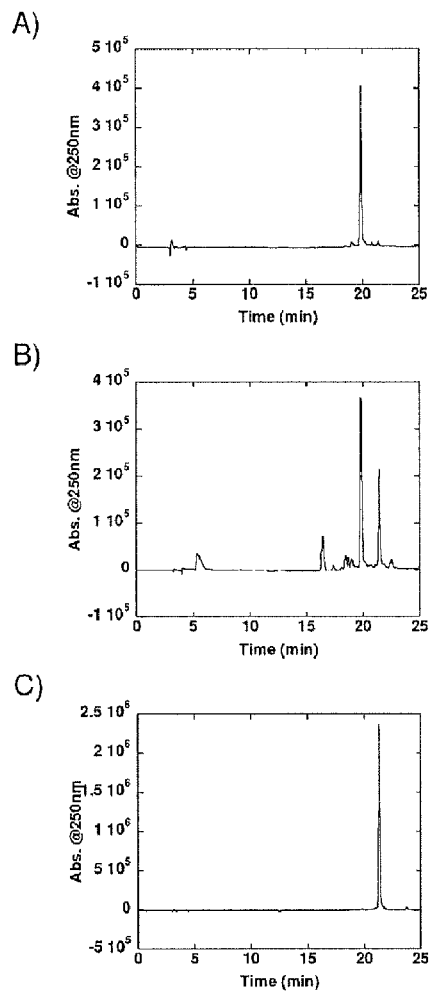
FIG. 3 shows the results of the reaction of APC with hypochlorous acid analyzed by HPLC. The graphs show the results for (A) APC, (B) reaction product of APC with hypochlorous acid, and (C) calcein.

The results of this analysis were shown in FIG. 3. The elution peak of APC was observed at about 19.8 minutes (FIG. 3, A), and the elution peak of calcein was observed at about 21.5 minutes (FIG. 3, C). For the reaction mixture of APC and hypochlorous acid, the elution peak of unreacted APC was confirmed at about 19.8 minutes, and the elution peak of calcein produced by the reaction with hypochlorous acid was also confirmed at about 21.5 minutes (FIG. 3, B). Therefore, it was confirmed that the increase of fluorescence intensity was due to generation of calcein produced by the reaction with reactive oxygen species. Calcein emits intense fluorescence in water, of which intensity is comparable to that of fluorescein, and shows extremely high intracellular retentivity much higher than that of fluorescein. Therefore, the compound of the present invention enables highly sensitive measurement of a trace amount of reactive oxygen species in cells over a long period of time.

Example 4

Figure 4:
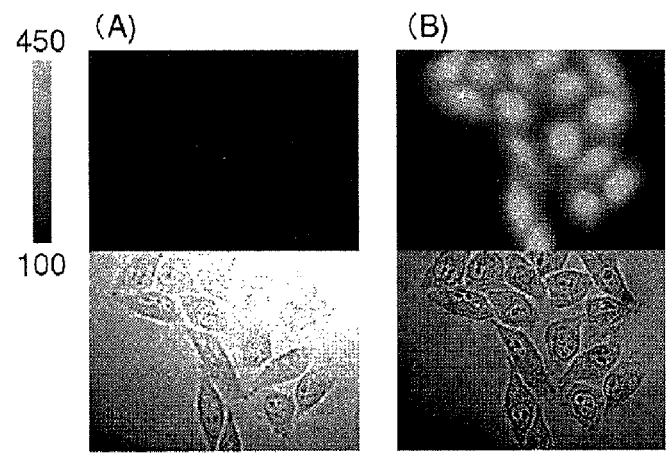
FIG. 4 shows the results obtained by applying APC-AM to the HeLa cells. The photographs show (A) the results obtained before sodium hypochlorite stimulation, and (B) the results obtained after sodium hypochlorite stimulation.

Imaging of reactive oxygen species in living cells was performed by using the compound 5 (APC). The compound 6 (APC-AM, 1.0 μM, 0.1% dimethylformamide (cosolvent)), which corresponds to APC esterified to increase cell membrane permeability, was loaded on the HeLa cells for 15 minutes by addition to the medium of the cells, and then the cells were stimulated with 500 μM sodium hypochlorite. (A) shows the result obtained before the sodium hypochlorite stimulation, and (B) shows the result obtained after the sodium hypochlorite stimulation. Extremely intense fluorescence was observed after the sodium hypochlorite stimulation, and accordingly, it was confirmed that APC-AM was noninvasively introduced into the cells, and then hydrolyzed to generate APC in the cells, and this APC reacted with hypochlorous acid to emit the extremely intense fluorescence (FIG. 4). This result demonstrated that the compound of the present invention is useful also in the fluorescence imaging of reactive oxygen species such as hypochlorous acid in living cells.

Example 5

Figure 5:
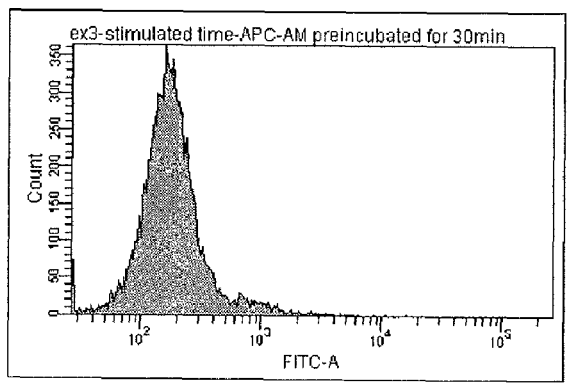
FIG. 5 shows the results of detection of reactive oxygen species using HL-60. The graphs show (A) the results obtained before hydrogen peroxide stimulation, (B) the results obtained without hydrogen peroxide stimulation, and (C) the results obtained with hydrogen peroxide stimulation.
Figure 5:
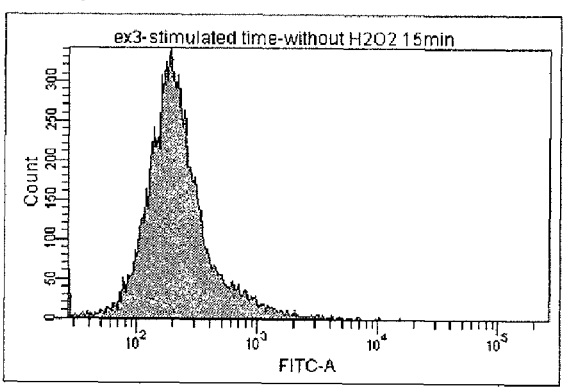
Figure 5:
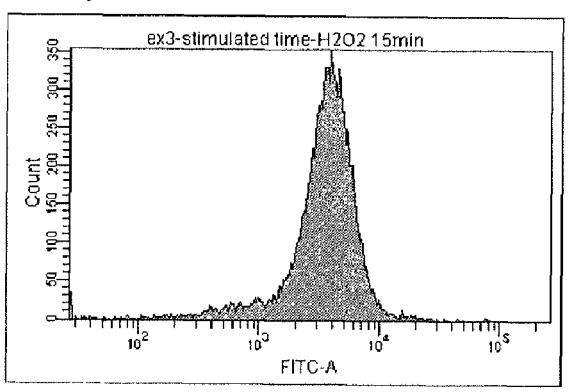

The compound 5 (APC) of the present invention and the conventional fluorescent probe, aminophenylfluorescein (APF), were applied to the HL-60 cells to compare reactivity thereof with reactive oxygen species and intracellular retentivity of the reaction products. It is known that the HL-60 cell is a hemocyte type floating cell, and has a myeloperoxidase, and therefore hydrogen peroxide and a chlorine ion react within the cell to generate hypochlorous acid. APC-AM (10 μM, 1.0% dimethylformamide (cosolvent)), which corresponds to APC in a form for incorporation into cells, was added to the medium and thereby loaded on the HL-60 cells for 60 minutes, then the cells were pre-incubated for 30 minutes, and stimulated with 100 μM hydrogen peroxide for 15 minutes, and then fluorescence intensity was measured by FACS (fluorescence activated cell sorting). The results are shown in FIG. 5. The graph (A) shows the results obtained for HL-60 cells before hydrogen peroxide stimulation, (B) shows the results obtained for HL-60 cells left for 15 minutes without hydrogen peroxide stimulation, and (C) shows the results obtained for HL-60 cells at 15 minutes after the hydrogen peroxide stimulation. There was no significant difference between the results of (A) and (B), and fluorescence intensity increased more than 20 times only in (C) for which hydrogen peroxide stimulation was performed. Therefore, it was demonstrated that the reactive oxygen species produced by the HL-60 cells could be made measurable by FACS by reacting it with APC.

Figure 6:
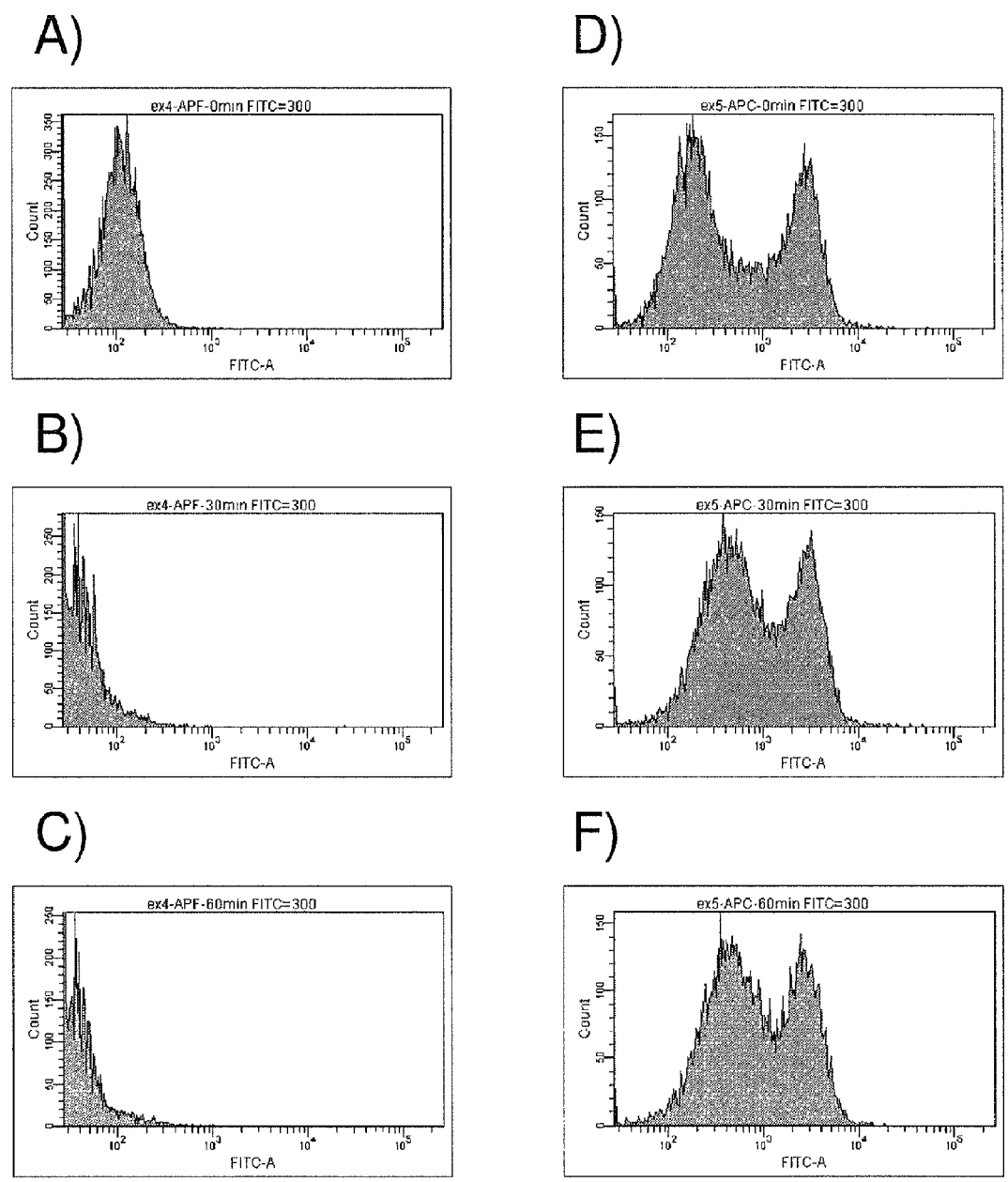
FIG. 6 shows the results of examination of reactivity with reactive oxygen species and intracellular retentivity performed by using APF and APC-AM. Among the graphs, the graphs (A) to (C) show the results obtained with APF, and the graphs (D) to (F) show the results obtained with APC-AM. The graphs (A) and (D) show the results obtained immediately after hydrogen peroxide stimulation, (B) and (E) show the results obtained 30 minutes after the stimulation, and (C) and (F) show the results obtained 60 minutes after the stimulation.

Intracellular retentivities of the reaction products produced from APF and APC with the reactive oxygen species were compared in a similar manner. APF and APC-AM (10 μM, 1.0% dimethylformamide (cosolvent) for the both) were loaded on the HL-60 cells for 60 minutes by adding them to the medium of the cells, and then the cells were stimulated with 100 μM hydrogen peroxide for 15 minutes. Then, fluorescence intensity was periodically measured (0 minute, 30 minutes, 60 minutes) by FACS. The results are shown in FIG. 6. In FIG. 6, the graphs (A) to (C) show the results obtained with APF, and the graphs (D) to (F) show the results obtained with APC-AM. The graphs (A) and (D) show the results obtained immediately after the hydrogen peroxide stimulation, (B) and (E) show the results obtained 30 minutes after the stimulation, and (C) and (F) show the results obtained 60 minutes after the stimulation. As for fluorescein produced by the reaction of APF with the reactive oxygen species, it was confirmed that the fluorescein stayed in the cells immediately after the stimulation, because increase of fluorescence intensity was observed at that time (A), but the fluorescein quickly leaked out of the cells after the reaction, and detection thereof became difficult after 30 minutes (B, C). In contrast, calcein produced by the reaction of APC, which was produced by hydrolysis of APC-AM in the cells, with the reactive oxygen species showed no change of fluorescence intensity from the level observed immediately after the stimulation, and thus it was confirmed that calcein was retained in the cells for a long period of time. Therefore, it was demonstrated that a trace amount of reactive oxygen species (especially a trace amount of reactive oxygen species in cells) was successfully detected with APC with high sensitivity over a long period of time.

INDUSTRIAL APPLICABILITY

The reagent for measurement of reactive oxygen containing the compound of the present invention and the method for measurement of reactive oxygen utilizing the aforementioned compound are useful as a regent and measurement method for measurement of especially reactive oxygen localizing in specific cells or tissues in living bodies with high sensitivity by a bioimaging technique.

What is claimed is:

1. A compound represented by the following formula (I):

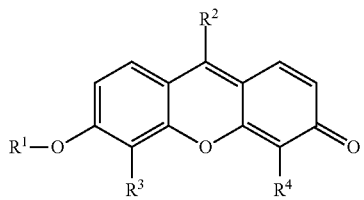

wherein $R^1$ represents an aryl group which may be substituted, $R^2$ represents a 2-carboxyphenyl group which may be substituted, and $R^3$ and $R^4$ independently represent a group represented as $—(CH_2)_p—N(R^5)(R^6)$ (in the formula, p represents an integer of 1 to 4, and $R^5$ and $R^6$ independently represent $—(CH_2)_n—COOH$ (in the formula, n represents an integer of 1 to 4)), a salt thereof, or an ester thereof.

2. The compound, a salt thereof, or an ester thereof according to claim 1, wherein $R^1$ is p-aminophenyl group or p-hydroxyphenyl group.

3. The compound, a salt thereof, or an ester thereof according to claim 1, wherein $R^2$ is 2-carboxyphenyl group.

4. The compound, a salt thereof, or an ester thereof according to claim 1, wherein $R^3$ and $R^4$ represent $—(CH_2)—N[(CH_2)—COOH]_2$.

5. An ester of the compound according to claim 1, which is a tetracetoxymethyl ester formed with $R^3$ or $R^4$.

6. A reagent for measurement of reactive oxygen, which contains the compound, a salt thereof, or an ester thereof according to claim 1.

7. The reagent according to claim 6, wherein the reactive oxygen species is hydroxyl radical, peroxynitrite, or hypochlorous acid.

8. The compound, a salt thereof, or an ester thereof according to claim 2, wherein $R^2$ is 2-carboxyphenyl group.

9. The compound, a salt thereof, or an ester thereof according to claim 2, wherein $R^3$ and $R^4$ represent $—(CH_2)—N[(CH_2)—COOH]_2$.

10. The compound, a salt thereof, or an ester thereof according to claim 3, wherein $R^3$ and $R^4$ represent $—(CH_2)—N[(CH_2)—COOH]_2$.

11. An ester of the compound according to claim 2, which is a tetracetoxymethyl ester formed with $R^3$ or $R^4$.

12. An ester of the compound according to claim 3, which is a tetracetoxymethyl ester formed with $R^3$ or $R^4$.

13. An ester of the compound according to claim 4, which is a tetracetoxymethyl ester formed with $R^3$ or $R^4$.

14. A reagent for measurement of reactive oxygen, which contains the compound, a salt thereof, or an ester thereof according to claim 2.

15. A reagent for measurement of reactive oxygen, which contains the compound, a salt thereof, or an ester thereof according to claim 3.

16. A reagent for measurement of reactive oxygen, which contains the compound, a salt thereof, or an ester thereof according to claim 4.

17. A reagent for measurement of reactive oxygen, which contains the compound, a salt thereof, or an ester thereof according to claim 5.

18. A reagent for measurement of reactive oxygen, which contains the compound, a salt thereof, or an ester thereof according to claim 8.

19. A reagent for measurement of reactive oxygen, which contains the compound, a salt thereof, or an ester thereof according to claim 9.

20. A reagent for measurement of reactive oxygen, which contains the compound, a salt thereof, or an ester thereof according to claim 10.

* * * * *